United States Patent
Yamamoto et al.

(10) Patent No.: US 9,125,961 B2
(45) Date of Patent: Sep. 8, 2015

(54) ION GENERATING UNIT AND ELECTRIC DEVICE

(71) Applicant: SHARP KABUSHIKI KAISHA, Osaka-shi, Osaka (JP)

(72) Inventors: Akira Yamamoto, Osaka (JP); Yasutaka Kataoka, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 0 days.

(21) Appl. No.: 14/349,508

(22) PCT Filed: Oct. 5, 2012

(86) PCT No.: PCT/JP2012/075890
§ 371 (c)(1),
(2) Date: Apr. 3, 2014

(87) PCT Pub. No.: WO2013/069395
PCT Pub. Date: May 16, 2013

(65) Prior Publication Data
US 2014/0231665 A1    Aug. 21, 2014

(30) Foreign Application Priority Data
Nov. 11, 2011   (JP) ................................. 2011-247925

(51) Int. Cl.
*G21K 5/04*     (2006.01)
*A61L 9/22*     (2006.01)
*H01T 23/00*    (2006.01)

(52) U.S. Cl.
CPC .. *A61L 9/22* (2013.01); *H01T 23/00* (2013.01)

(58) Field of Classification Search
USPC ........... 250/423 R, 424, 425, 426, 427, 423 P, 250/423 F; 315/111.81, 111.91
See application file for complete search history.

(56) References Cited

U.S. PATENT DOCUMENTS

| | | |
|---|---|---|
| 2011/0133098 A1 | 6/2011 | Kitagaito et al. |
| 2011/0174969 A1* | 7/2011 | Seyfarth ........................ 250/288 |
| 2012/0037799 A1* | 2/2012 | Sakairi .......................... 250/288 |

FOREIGN PATENT DOCUMENTS

| | | |
|---|---|---|
| JP | 2010-62036 A | 3/2010 |
| WO | 2010/024318 A1 | 3/2010 |

* cited by examiner

*Primary Examiner* — Nicole Ippolito
(74) *Attorney, Agent, or Firm* — Birch, Stewart, Kolasch & Birch, LLP

(57) ABSTRACT

An ion generating unit includes: a box-like housing with its one face open, an ion generating part provided with electrode parts and generating positive and negative ions; an ion sensor; a lid covering the housing in a removable manner while the ion generating unit is accommodated in the housing; a cover covering the housing in such a manner that cannot be easily removed while the ion sensor is accommodated in the housing; a connector provided at one end of the housing for mechanically and electrically connecting the ion generating unit; and a screw part provided at the other end of the housing for securing the ion generating unit to the casing.

6 Claims, 11 Drawing Sheets

F I G. 11
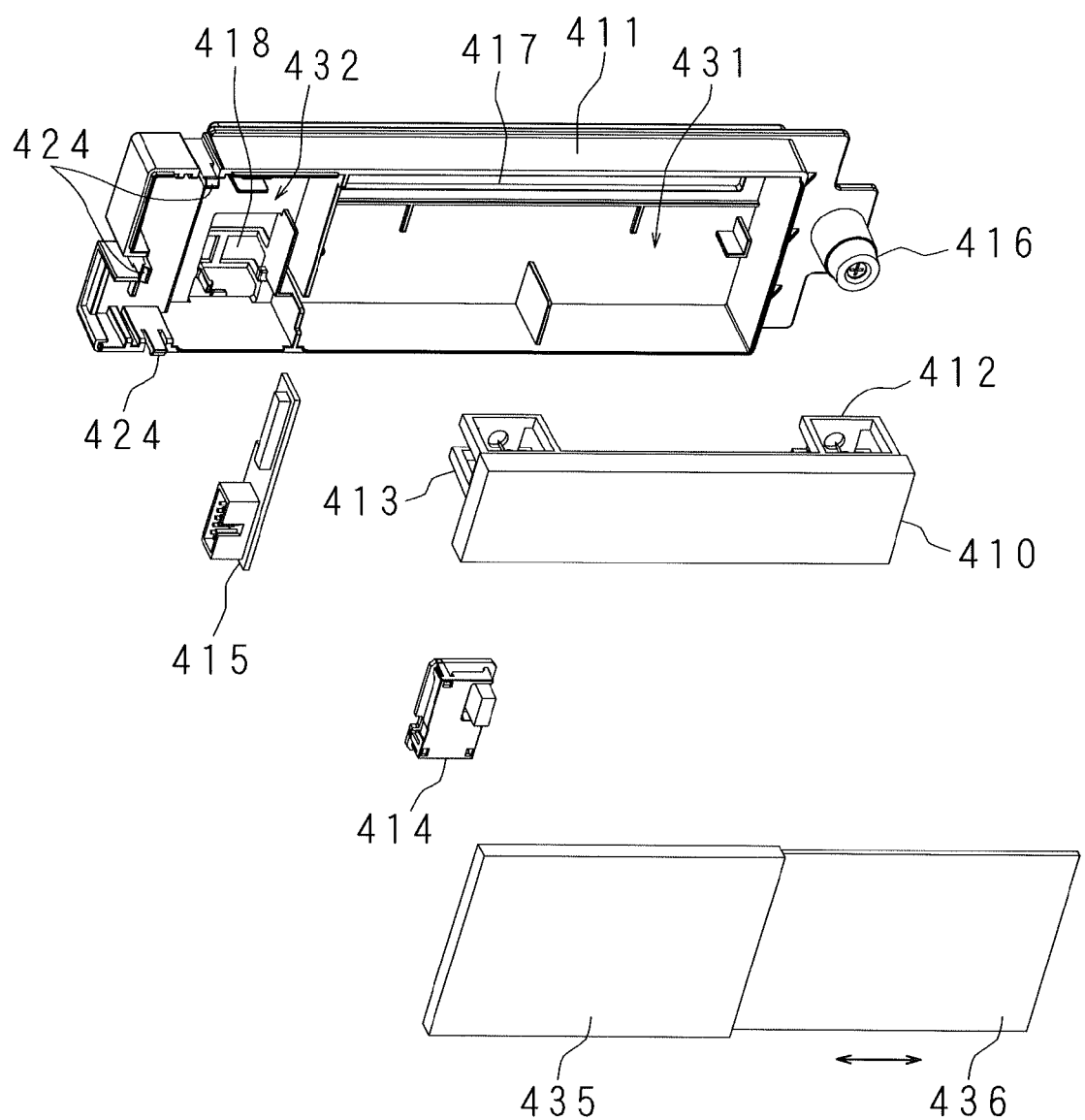

ION GENERATING UNIT AND ELECTRIC DEVICE

CROSS-REFERENCE TO RELATED APPLICATIONS

This non-provisional application is a National Stage entry under U.S.C. §371 of International Application No. PCT/JP2012/075890 filed on Oct. 5, 2012, which claims priority to Japanese Patent Application No. 2011-247925 filed in Japan on Nov. 11, 2011. The entire contents of all of the above applications are hereby incorporated by reference.

BACKGROUND

The present invention relates to an ion generating unit generating ions and an electric device provided with an ion generating unit.

DESCRIPTION OF RELATED ART

Conventionally, an air purifier or an air conditioner has been realized, which is able to deodorize or sterilize, for example, a wall surface in a room by generating steam from liquid having a deodorizing function and/or a sterilizing function and diffusing the steam in the room by airflow generated using a fan.

Such an air purifier or air conditioner is provided with an ion generator. The ion generator is, for example, housed in a casing having a shape of a substantially rectangular-parallelepiped, and includes an ion generating part generating positive and negative ions separately from each other in the direction intersecting the airflow. Moreover, an ion sensor is also included near the ion generating unit (see Japanese Patent Application Laid-Open No. 2010-62036).

SUMMARY

In the ion generator as disclosed in Japanese Patent Application Laid-Open No. 2010-62036, however, the ion generating part and the ion sensor are integrally formed, which requires replacement of the entire ion generator if abnormality occurs in, for example, the ion generating part. Since the entire ion generator has to be replaced even when the ion sensor is not defective, resulting in unnecessarily high cost.

The present invention has been devised in view of the circumstances described above. An object of the invention is to provide an ion generating unit in which an ion generating part can be replaced without replacing an ion sensor, and an electric device including the ion generating unit.

An ion generating unit according to the present invention, provided with a housing accommodating an ion generating part and an ion sensor detecting an ion generated at the ion generating unit, is characterized by including an opening configured to remove the ion generating part from the housing without exposure of the ion sensor.

In the present invention, an opening is formed for removing the ion generating part from the housing without exposure of the ion sensor. If abnormality occurs in the ion generating part while the ion sensor operates normally, the ion generating part is removed through the opening without exposure of the ion sensor and is replaced. Thereafter, the ion generating part is inserted into the opening to be attached to the housing and the ion generating unit with the replaced ion generating part is mounted to the ion generating apparatus. This allows only the ion generating part to be replaced without replacement of a normal ion sensor, thereby preventing the cost from unnecessarily increasing.

The ion generating unit according to the present invention is characterized by further including a lid configured to cover the opening in such a manner as to be removable or opened/closed.

In the present invention, a lid is provided which covers the opening and which is removable or can be opened and closed. For example, the lid can be attached to the housing with a screw or the like in such a manner that it can easily be removed. Alternatively, the lid may be fixed rotatably to the housing with a hinge or the like so as to be opened and closed. It is also possible for the lid to be slidably attached so that the opening can be opened and closed, and the lid may slide to open and close the opening. If abnormality occurs in the ion generating part while the ion sensor operates normally, the lid is removed from the housing or opened and closed to replace the ion generating part without the ion sensor being exposed, and thereafter the lid is attached to the housing or the opening is closed and the ion generating unit with the replaced ion generating part is mounted to the ion generating apparatus. This allows only the ion generating part to be replaced without replacement of a normal ion sensor, thereby preventing the cost from unnecessarily increasing.

The ion generating unit according to the present invention is characterized by further including a cover configured to cover the housing in which the ion sensor is accommodated in such a manner as not to be easily removed or easily opened and closed.

In the present invention, a cover is provided which covers the housing in which the ion sensor is accommodated in such a manner that is not easily removed or opened/closed. For example, the cover is provided with a fitting member while the housing is provided with a receiving member so that the cover cannot easily be removed from the housing or be opened and closed. If abnormality occurs at the ion generating part while the ion sensor operates normally, the lid is removed from the housing and the ion generating part is replaced, and thereafter the lid is attached to the housing and then the ion generating unit with the replaced ion generating part is mounted to the ion generating apparatus. This allows only the ion generating part to be replaced without replacement of a normal ion sensor, thereby preventing the cost from unnecessarily increasing.

The ion generating unit according to the present invention is characterized in that the ion generating part has an electrode for generating ions, the ion sensor has a sensor plane for detecting ions, and the housing accommodates the ion sensor with the sensor plane exposed at a part of the housing, and accommodates the ion generating part with the electrode protruding from the part.

In the present invention, the ion generating part has an electrode for generating ions. The ion sensor has a sensor plane for detecting ions. The housing accommodates the ion sensor therein with the sensor plane exposed at a part of the housing, and accommodates the ion generating part with the electrode protruding from a part of the housing. A part of the housing here corresponds to, for example, a plane defining the contour of the housing. That is, the sensor plane is exposed while the electrode protrudes from a part (a plane) of the housing. The protruding electrode facilitates generation of ions as well as discharge of the generated ions. Furthermore, the sensor plane of the ion sensor is exposed to a plane of the housing, so that the plane of the housing and the sensor plane may be arranged in plane with each other, preventing the ion sensor from obstructing the flow of air.

The ion generating unit according to the present invention is characterized in that the ion generating part is provided with an electrode for generating a positive ion and an electrode for generating a negative ion separated from each other, and the ion sensor is so provided that a virtual line defining a spacing distance between the ion sensor and one electrode for ion detection has an angle larger than 90 degrees but smaller than 180 degrees with respect to a virtual line defining a spacing distance between said one electrode and another electrode.

In the present invention, the ion generating part is provided with an electrode for generating positive ions and an electrode for generating negative ions separated from each other. The ion sensor is so arranged that a virtual line defining the spacing distance between the ion sensor and one electrode for ion detection (the electrode for generating negative ions, for example) and a virtual line defining the spacing distance between the above-described one electrode and another electrode (the electrode for generating positive ions, for example) have an angle with respect to each other larger than 90 degrees but smaller than 180 degrees. The spacing distance corresponds to, for example, the distance between the electrodes and the distance between the center of the ion sensor (center of the sensor plane) and an electrode. The virtual line may be, for example, a straight line projected on a plane vertically intersecting an electrode. The angle may be, for example, approximately between 100 and 140 degrees.

According to the configuration described above, for example, the ion sensor may be located close to one electrode and away from the other electrode. Furthermore, the angle being 90 degrees or larger allows the ion sensor to be located in a diagonally downward direction from one electrode for ion detection (the electrode for generating negative ions, for example) without being located directly below the electrode. Accordingly, even when the direction of the air flowing out from a fan is not in the vertical (longitudinal) direction but in a direction diagonal to the vertical direction, the ion sensor can be disposed at the downstream side of the electrode for ion detection along the direction of air, while being away from the electrode not for ion detection (the electrode for generating positive ions, for example). Thus, the concentration of ions may precisely be detected.

An electric device according to the present invention is characterized by including the ion generating unit according to any one of the aspects of the invention described above, and in that the ion generated at the ion generating unit is discharged from an outlet.

In the present invention, such an electric device can be realized that only the ion generating part may be replaced without replacement of a normal ion sensor and thus unnecessary increase in cost can be prevented.

According to the present invention, an ion generating part can be replaced without replacing a normal ion sensor, thereby preventing the cost from unnecessarily increasing. The above and further objects and features of the invention will more fully be apparent from the following detailed description with accompanying drawings.

BRIEF DESCRIPTION OF DRAWINGS

FIG. 11 is an exploded perspective view as the fourth example of the ion generating unit according to an embodiment of the invention.

DETAILED DESCRIPTION

Figure 1:
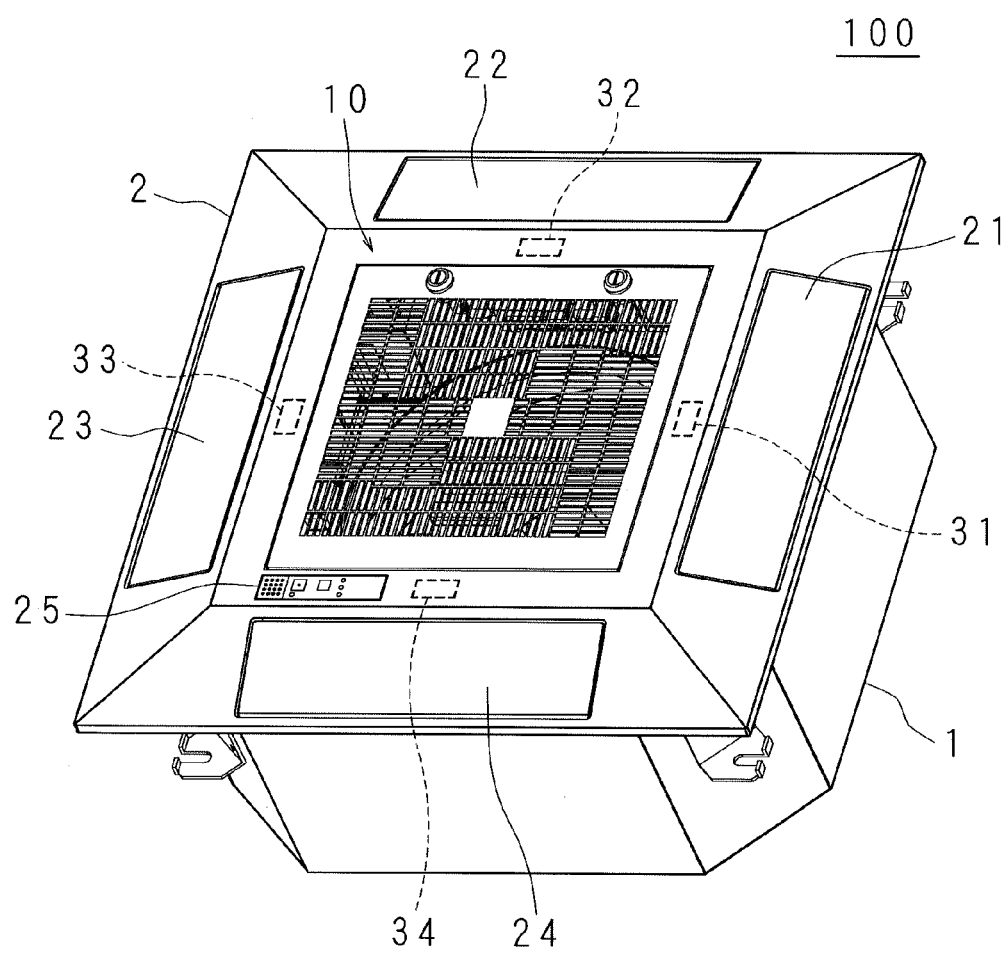
FIG. 1 is an appearance perspective view illustrating a configuration example of an ion generating apparatus according to an embodiment of the invention in a state where louvers are closed.
Figure 2:
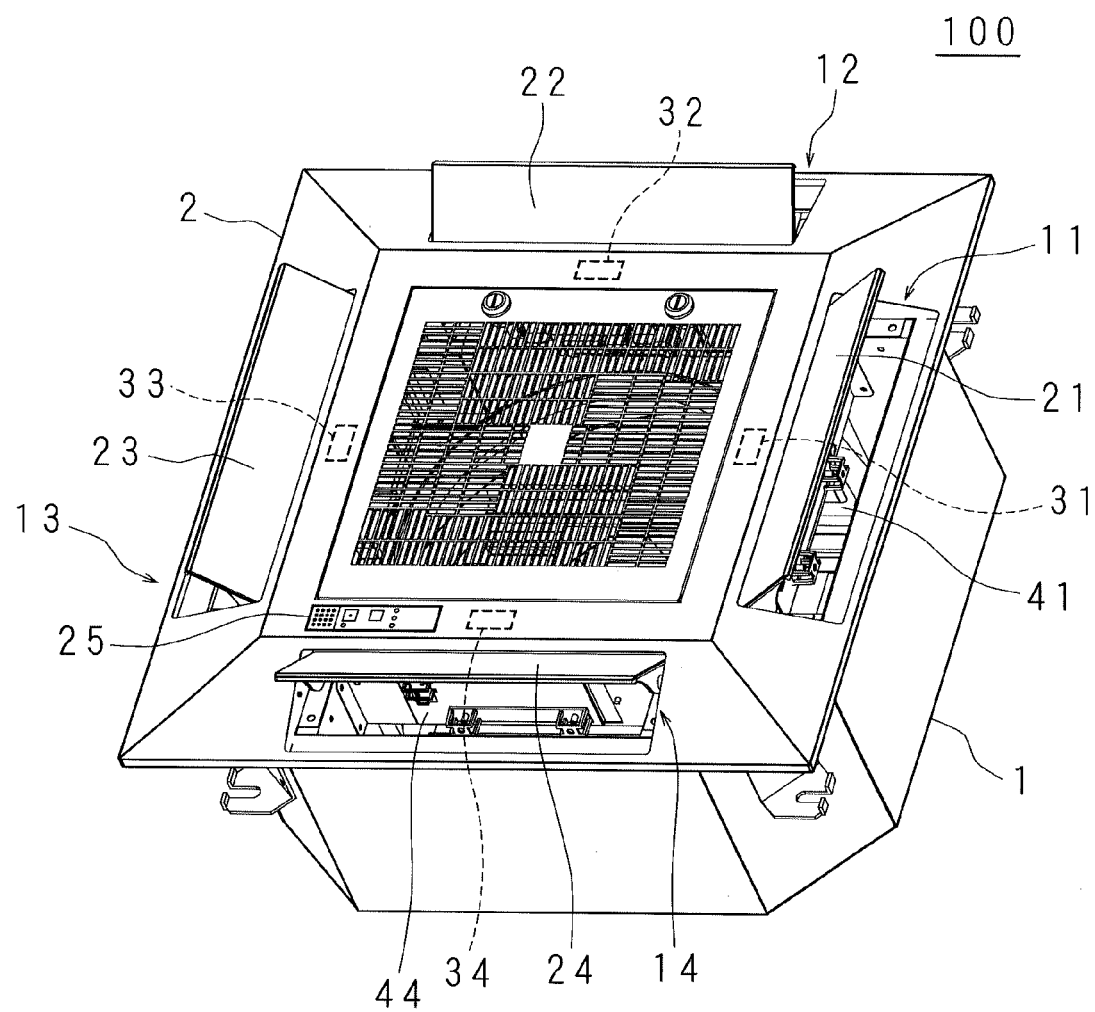
FIG. 2 is an appearance perspective view illustrating a configuration example of an ion generating apparatus according to an embodiment of the invention in a state where louvers are opened.
Figure 3:
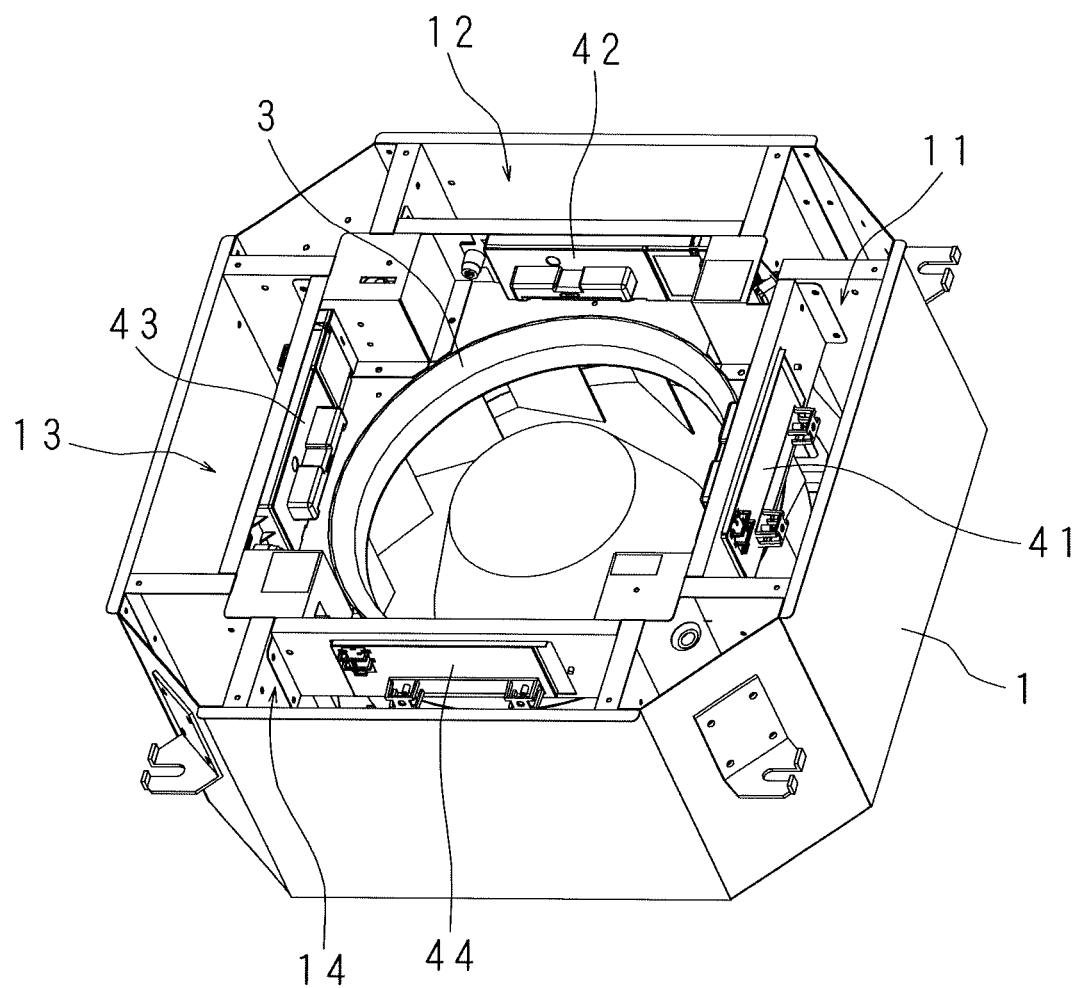
FIG. 3 is a perspective view illustrating an example of an internal configuration of an ion generating apparatus according to an embodiment of the invention.

The present invention will now be described below with reference to the drawings illustrating the embodiment thereof. FIG. 1 is an appearance perspective view illustrating an example of a configuration of an ion generating apparatus 100 according to the present embodiment in a state where louvers are closed; FIG. 2 is an appearance perspective view illustrating an example of a configuration of the ion generating apparatus 100 according to the present embodiment in a state where louvers are opened; and FIG. 3 is a perspective view illustrating an example of an internal configuration of the ion generating apparatus 100 according to the present embodiment. The ion generating apparatus 100 includes a box-like casing 1 with one plane open, a rectangular panel 2 attached to the open plane of the casing 1, and so forth. While an ion generating apparatus is described as an example of an electric device in the description below, the electric device is not limited to the ion generating apparatus but may also include, for example, an air purifier, an air conditioner, a fan heater, a humidifier, a dehumidifier, a refrigerator and a sterilizer.

The panel 2 is provided with, at the middle part thereof, a rectangular inlet 10 for taking in the air. The area where the inlet 10 is formed has a larger dimension in height (thickness), while the surface (front face) of the panel 2 is inclined with respect to the plane of the inlet 10 so as to have the dimension in height decreasing from the middle part toward the circumference of the panel 2.

Rectangular air outlets 11, 12, 13 and 14 are formed at the rims of the panel 2. Moreover, each of the outlets 11 through 14 are provided with louvers 21, 22, 23 and 24, which are air-direction adjustment plates, respectively.

Each of the louvers 21 to 24 has a rectangular shape having substantially the same dimensions as those of the outlets 11 to 14. The louvers 21 to 24 are so provided as to be rotatable around the axis along the edges of the outlets 11 to 14 on the sides opposite from the respective rims of the panel 2. The rotating operation of each of the louvers 21 to 24 is controlled by a louver control circuit 58, which will be described later. By closing the louvers 21 to 24, the outlets 11 to 14 are covered by the louvers 21 to 24. Moreover, by opening the louvers 21 to 24 with an appropriate angle (e.g., an angle with respect to the inlet 10), the air including ions blown out from the outlets 11 to 14 may hit the inner side surfaces of the louvers 21 through 24, to be adjusted for its direction. Furthermore, the air including ions blown out from the outlets 11 to 14 may flow out in the direction from the middle part of the panel 2 toward the rims.

Near the outlets 11 to 14, LEDs 31, 32, 33 and 34 are located as display parts, which correspond to the respective outlets 11 to 14. The LEDs 31 to 34 may be, for example, located between the circumferential edge of the inlet 10 and the end of each of the outlets 11 to 14.

Each of the LEDs 31 to 34 may also be provided with a light guiding member (not illustrated) such that the light when turned on can illuminate a desired region on the outer side surface of each of the louvers 21 to 24. This allows a desired region on the outer side surfaces of the louvers 21 to 24 to be illuminated regardless of the state of the louvers 21 to 24, i.e. whether they are open or closed, thereby enhancing the external visibility.

On the front face of the panel 2, a display panel 25 is disposed, which is provided with, for example, an LED light as a reporting part for reporting occurrence of abnormality, a light receiving part as an obtaining part for obtaining a predetermined signal from an external device such as a remote control.

For example, the display panel 25 is provided with multiple LED lights, including an LED light (operation light) indicating that the ion generating apparatus 100 is in operation, an LED light for urging the user to replace an ion generating unit, which will be described later, an LED light reporting abnormality of the ion generating unit or the like, and an LED light for urging the user to clean the ion generating unit, a filter (not illustrated) or the like.

As illustrated in FIG. 2 or FIG. 3, ion generating units 41, 42, 43 and 44 are mounted inside the outlets 11 to 14, respectively.

Furthermore, as illustrated in FIG. 3, a fan 3 is placed at the middle part of the casing 1. The fan 3 is a so-called turbo fan, which includes multiple blades standing in the direction of the rotation axis. The blades are inclined along the circumferential direction of the fan 3. In other words, the distance from the rotation axis of the fan 3 to one end of each blade is different from that to the other end thereof. As the fan 3 rotates, the blades push the air to the outside. Accordingly, as the fan 3 rotates, the air is taken in from the inlet and the taken-in air is discharged from each of the outlets 11 to 14 while including ions.

Figure 4:
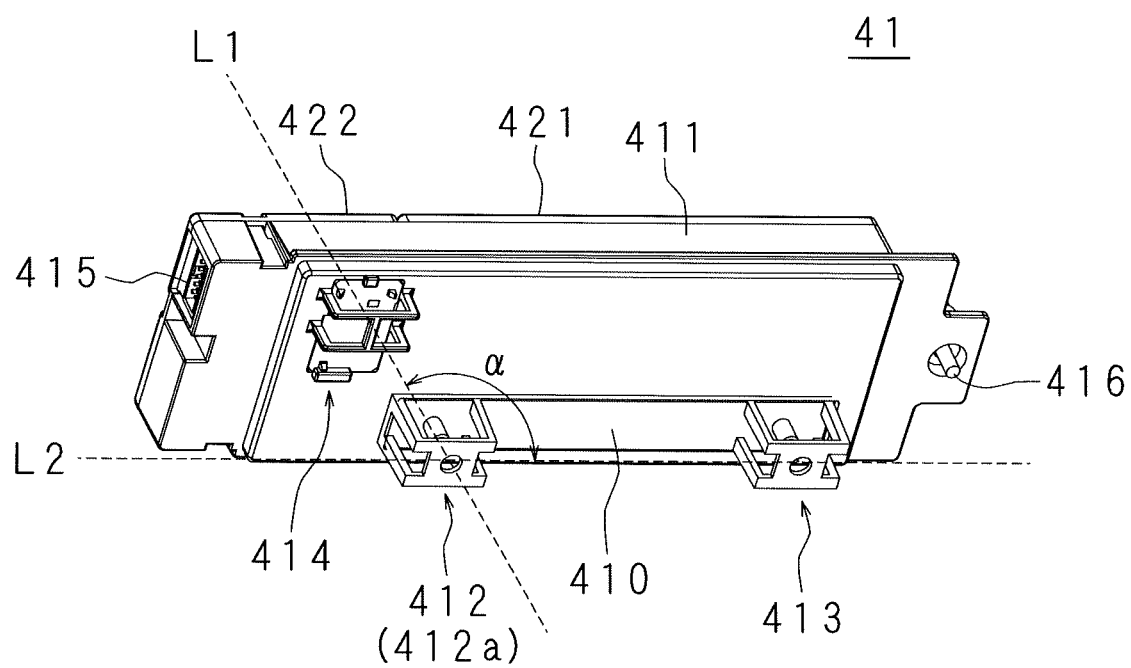
FIG. 4 is an appearance perspective view illustrating an example of an ion generating unit according to an embodiment of the invention.
Figure 5:
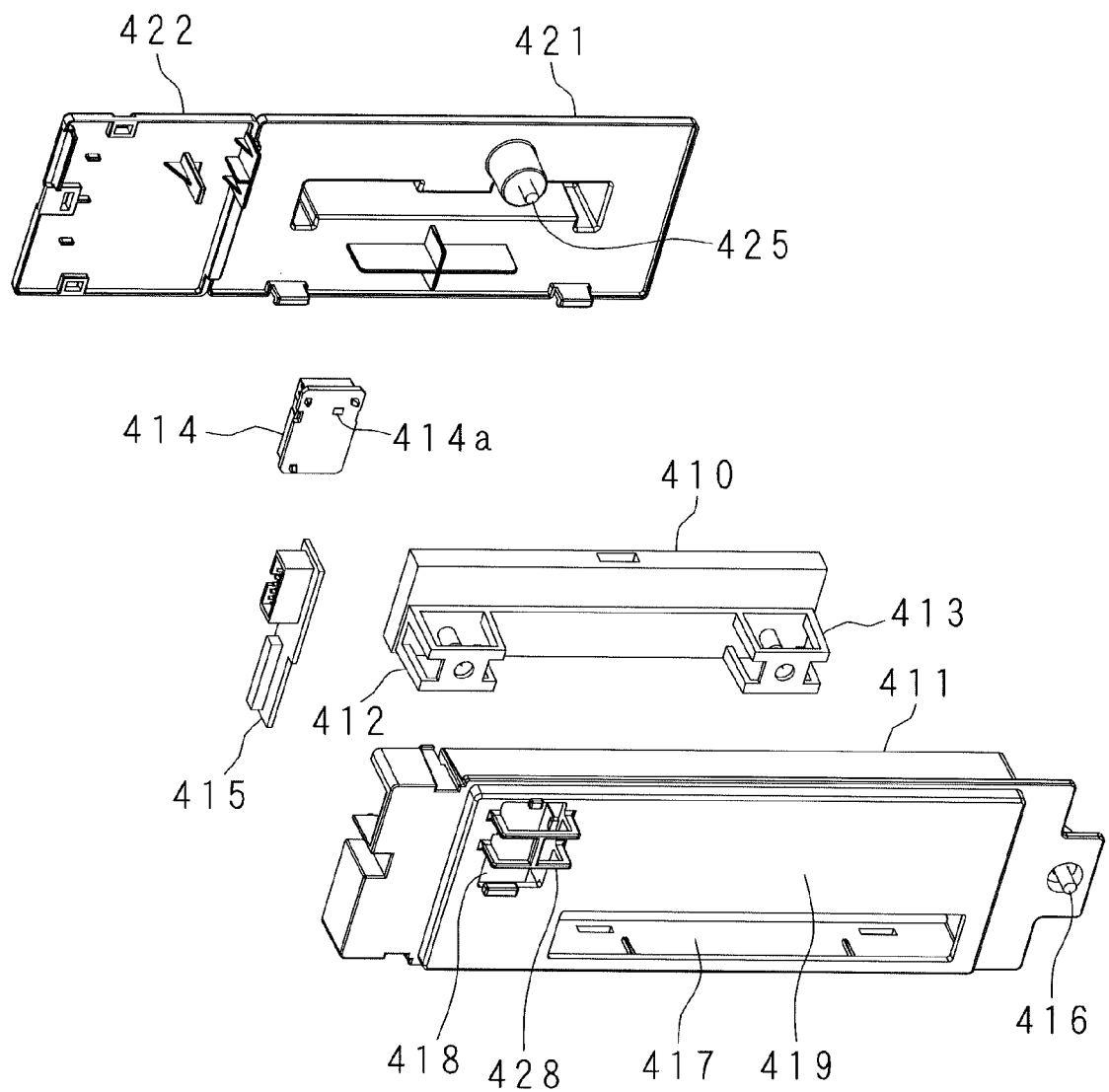
FIG. 5 is an exploded perspective view from the side of a housing of the ion generating unit according to an embodiment of the invention.
Figure 6:
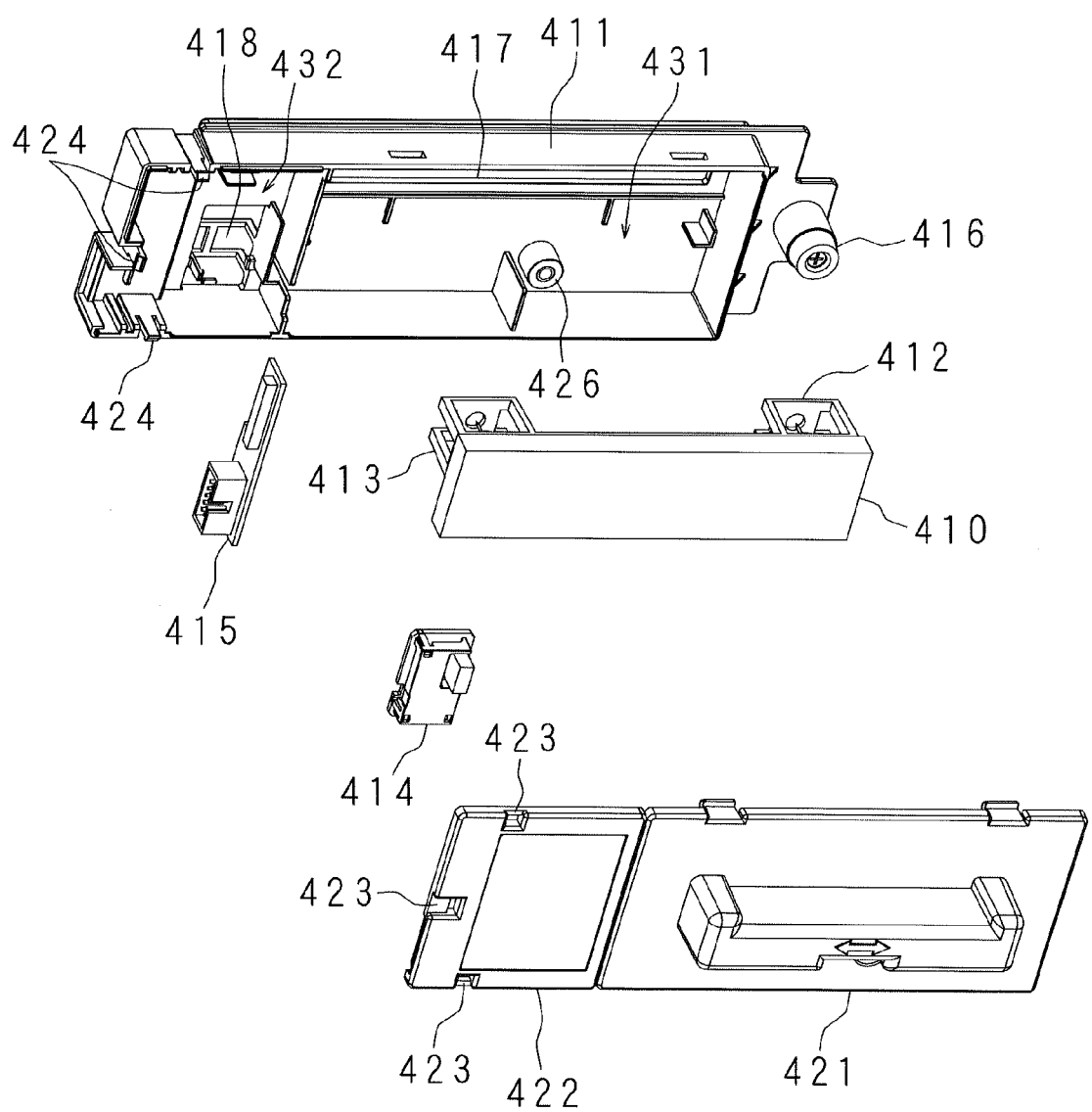
FIG. 6 is an exploded perspective view from the side of a lid as the first example of the ion generating unit according to an embodiment of the invention.
Figure 7:
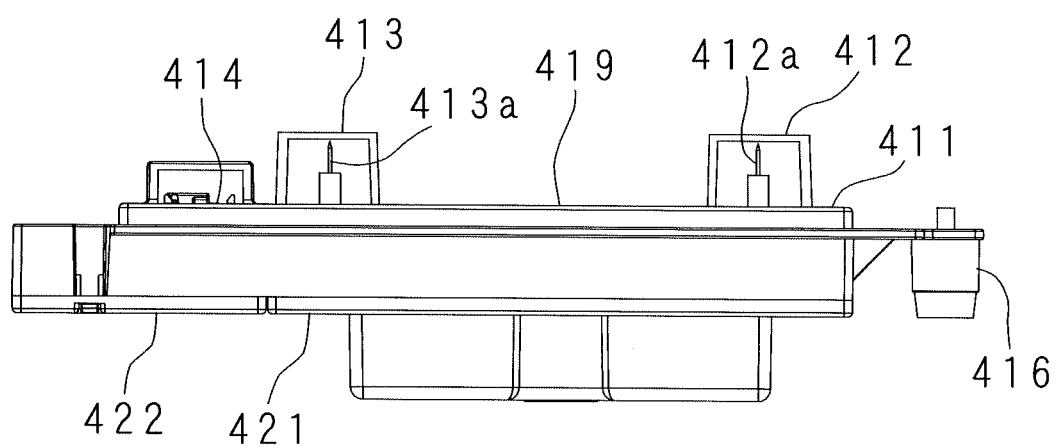
FIG. 7 is a side view illustrating an example of the ion generating unit according to an embodiment of the invention.

FIG. 4 is an appearance perspective view illustrating an example of an ion generating unit 41 according to the present embodiment; FIG. 5 is an exploded perspective view from the side of a housing 411 of the ion generating unit 41 according to the present embodiment; FIG. 6 is an exploded perspective view from the side of a lid 421 as the first example of the ion generating unit 41 according to the present embodiment; and FIG. 7 is a side view illustrating an example of the ion generating unit 41 according to the present embodiment. Since the other ion generating units 42 through 44 are configured similarly to the ion generating unit 41, only the ion generating unit 41 will be described below.

As illustrated in FIG. 4, the ion generating unit 41 includes, for example, a box-like housing 411 with its one face open, an ion generating part 410 provided with electrode parts 413 and 412 generating positive and negative ions, an ion sensor 414, a lid 421 covering the housing 411 in a removable manner while the ion generating part 410 is accommodated in the housing 411, a cover 422 covering the housing 411 in a manner not easily removable while the ion sensor 414 is accommodated in the housing 411, a connector 415 located at one end of the housing 411 for mechanically and electrically connecting the ion generating unit 41, and a screw part 416 for securing the ion generating unit 41 to the casing 1.

The ion generating unit 410 has the shape of a rectangular plate, and is provided with the electrode part 412 generating negative ions near one end thereof and with the electrode part 413 generating positive ions near the other end thereof.

The ion generating unit 41 ionizes the moisture in the air by plasma discharge to generate $H^+ (H_2O)_n$ (n is an arbitrary natural number) as positive ions and $O_2^- (H_2O)_m$ (m is an arbitrary natural number) as negative ions. The generated compounds react chemically with each other to generate hydrogen peroxide ($H_2O_2$) and/or hydroxyl radical (OH), i.e. active species, thereby eliminating floating bacteria, floating virus or the like in the air.

Thus, each of the outlets 11 to 14 can blow out the air including positive ions and the air including negative ions separately from each other, which can avoid immediate neutralization of the positive and negative ions in the air blown out from the ion generating apparatus. By thus preventing the ions from being neutralized, the diffusion characteristics of ions can be enhanced.

At a bottom plate 419 of the housing 411, a substantially-rectangular opening 417 is formed so that each of the electrode parts 412 and 413 of the ion generating part 410 protrudes from the surface of the bottom plate 419.

Moreover, near a corner of the bottom plate 419, an opening 418 for exposing the ion sensor 414 (a sensor plane 414a of the ion sensor 414) so that the sensor plane 414a is in plane with a surface (one plane) of the bottom plate 419. The ion sensor 414 has, for example, a substantially-rectangular shape, while the opening 418 has a rectangular shape with substantially the same dimension as that of the ion sensor 414. Furthermore, at the area of the bottom plate 419 where the sensor plane 414a is exposed, a frame-like protection member 428 is disposed to prevent a hand from directly touching the ion sensor 414 or the sensor plane 414a.

The housing 411 has an accommodation space 431 for accommodating the ion generating part 410. The ion generating part 410 can be housed in the accommodation space 431 while each of the electrode parts 412 and 413 of the ion generating part 410 protrudes to the outside from the opening 417. It is noted that an appropriate member (screw, for example) may be used to secure the ion generating part 410.

While the ion generating unit 410 remains in the accommodation space 431 of the housing 411, a lid 421 for covering the housing 411 (more specifically, the ion generating part 410) may be attached. The lid 421 can be attached to be removable (easily removed) from the housing 411 by inserting a screw part 425 provided at the lid 421 into a screw hole 426, formed at the inner side surface of the bottom plate 419 of the housing 411, and fastening it.

It is noted that the lid 421 may be attached to the housing 411 also by means of another structure which makes the lid 421 easily removable, not limited to the manner using a screw and a screw hole.

Moreover, the housing 411 has an accommodation space 432 for accommodating the ion sensor 414. At the upper end of the side plate of the housing 411 defining the accommodation space 432, three projecting fitting parts 424 are formed for fitting the cover 422 to the housing 411. Furthermore, at the positions corresponding to the fitting parts 424 of the cover 422, fit holes 423 are formed as members to receive the fitting parts 424.

The cover 422 for covering the housing 411 (more specifically, ion sensor 414) may be attached while the ion sensor 414 remains in the accommodation space 432 of the housing 411. The cover 422 may be so attached as not to be easily removed from the housing 411 or opened/closed by fitting the projecting fitting parts 424 formed at the housing 411 into the respective fit holes 423 formed at the cover 422.

As described above, the lid 421 for removably covering the housing 411 in which the ion generating unit 410 is accommodated and the cover 422 covering, in a not-easily removable manner, the housing 411 accommodating the ion sensor 410. For example, the lid 421 may be attached to the housing 411 in a removable manner with a screw or the like. On the other hand, the cover 422 may be provided with, for example, fit holes 423 at the cover 422 and projecting fitting members at the housing 411 in such a manner that it cannot be easily removed from the housing 411. It is also possible to form a projecting fitting part at the cover 422 and a fit hole at the housing 411.

If abnormality occurs at the ion generating part 410 while the ion sensor 414 operates normally, after the lid 421 is removed from the housing 411 and the ion generating part 410 is replaced, the lid 421 is attached to the housing 411 and the ion generating unit 41 with the replaced ion generating part 410 is mounted to the ion generating apparatus 100. This allows only the ion generating part 410 to be replaced without replacement of the normal ion sensor 414, thereby preventing the cost from unnecessarily increasing.

It is noted that, for example, the cover 422 may be attached to the housing 411 also by means of another structure which makes the cover 422 not easily removable, not limited to the example as described above.

In the structure exemplified in FIGS. 4 to 6 as described above, the cover 422 is fitted to the housing 411. The present invention is, however, not limited thereto but may also have a structure not including the cover 422. In other words, the ion generating unit 41 may include the lid 421 alone instead of including both the lid 421 and the cover 422. In such a case, the lid 421 covers the housing 411 and may be removable without the exposure of the ion sensor 414.

If abnormality occurs at the ion generating part 410 while the ion sensor 414 operates normally, the lid 421 is removed from the housing 411 and the ion generating part 410 is replaced without the exposure of the ion sensor 414, and thereafter, the lid 421 is attached to the housing 411 and the ion generating unit 41 with the replaced ion generating part 410 is mounted to the ion generating apparatus 100. This allows only the ion generating part 410 to be replaced without replacement of the normal ion sensor 414, thereby preventing the cost from unnecessarily increasing.

Furthermore, the ion generating part 410 has needle electrodes 412a and 413a, as electrodes for generating ions, at the electrode parts 412 and 413 (see FIG. 7). In the description below, a needle electrode having the shape of a needle is described as an example of an electrode. The electrode is, however, not limited to the needle electrode but may also be, for example, a printed electrode discharging ions by creeping discharge. The ion sensor 414 has a sensor plane 414a for detecting ions. The housing 411 accommodates the ion sensor 414 with the sensor plane 414a exposed at a part of the housing 411 (more specifically, the surface of the bottom plate 419), while accommodating the ion generating part 410 with the needle electrodes 412a and 413a protruding from a part of the housing 411 (more specifically, the surface of the bottom plate 419). Note that the part of the housing corresponds to a plane defining the contour of the housing (more specifically, the surface of the bottom plate 419).

In other words, the needle electrodes 412a and 413a are formed to protrude from a part (a surface) of the housing 411 while the sensor plane 414a is exposed thereat. The protruding needle electrodes 412a and 413a facilitate generation of ions and discharge of the generated ions. Moreover, as the sensor plane 414a of the ion sensor 414 is exposed at one plane of the housing 411, the plane of the housing 411 (more specifically, the surface of the bottom plate 419) and the sensor plane 414a may be arranged in plane with each other, preventing the ion sensor 414 from obstructing the flow of air.

Furthermore, as illustrated in FIG. 4, the ion generating part 410 is so provided that the needle electrode 413a for generating positive ions and the needle electrode 412a for generating negative ions are separated from each other. The ion sensor 414 is so provided that a virtual line L1 defining the spacing distance between one needle electrode for ion detection (e.g., the needle electrode for generating negative ions) 412a and the ion sensor 414 has an angle α larger than 90 degrees but smaller than 180 degrees with respect to a virtual line L2 defining the spacing distance between the needle electrode 412a and the other needle electrode (e.g., the needle electrode for generating positive ions) 413a.

Here, the spacing distance corresponds to, for example, the distance between the needle electrodes 412a and 413a, or the distance between the center of the ion sensor 414 (center of the sensor plane 414a) and the needle electrode 412a. The virtual line may be, for example, a straight line projected on the plane vertically intersecting the needle electrodes 412a and 413a. The angle α may be, for example, approximately in the range of 100 to 140 degrees.

According to the structure described above, for example, it is possible to make the ion sensor 414 closer to one needle electrode 412a and also to make it away from the other electrode 413a. Moreover, the angle α of 90 degrees or larger allows the ion sensor 414 to be located in a diagonally downward direction from the needle electrode 412a, not directly below one needle electrode (e.g., needle electrode for generating negative ions) 412a for ion detection, when the needle electrodes 412a and 413a are arranged horizontally (in the lateral direction). Thus, in the case where the air is blown out from a fan not in the vertical (longitudinal) direction but in a direction diagonal to the vertical direction, the ion sensor 414 may be located at the downstream of the needle electrode 412a for ion detection along the direction of the air while the ion sensor 414 may be placed away from the needle electrode not for ion detection (e.g., the needle electrode for generating positive ions) 413a, thereby allowing precise detection of ion concentration.

Figure 8:
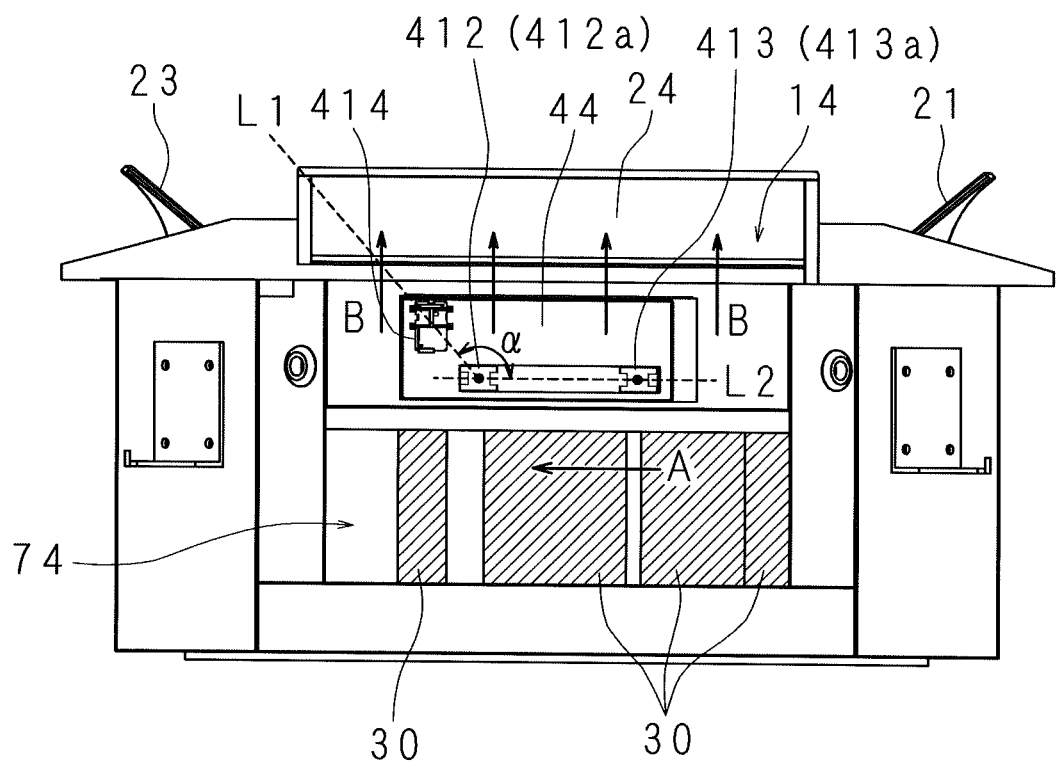
FIG. 8 is a section view of a main part illustrating an example of the inner side of an outlet.

FIG. 8 is a section view of a main part illustrating an example of the inner side of an outlet 14. Note that FIG. 8 illustrates a partially-broken section view in order to show the structure of the substantial part of the inside of the outlet 14. In the state where the ion generating apparatus 100 is attached to the ceiling, the upper side in FIG. 8 is directed downward in the vertical direction, while the lower side in FIG. 8 is on the ceiling side, i.e. directed upward in the vertical direction. In FIG. 8, the reference numeral 74 indicates a feed port. The feed port 74 communicates with the outlet 14, has substantially the same length as that of the outlet 14 as well as substantially the same height as that of the blades 30 of the fan 3. The feed port 74 is to guide the air coming out from the fan 3 to the electrode parts 412 and 413. Though three other feed ports, each having a structure similar to that of the feed port 74, are formed in addition to the feed port 74 for corresponding to the other outlets 11 through 13, the feed port 74 will be described below.

In FIG. 8, the blades 30 denoted by the reference numeral 30 are provided with pattern for convenience in order to distinguish them from other portions. Furthermore, the reference code A indicates the rotating direction of the fan 3, i.e. blades 30.

The air coming out from the fan 3 flows into the feed port 74, passes through the inside of the outlet 14 and flows out from the outlet 14. Then, the fan 3 blows out the air so as to discharge the ions generated at the ion generating part 410 from the outlet 14. The ion generating part 410 is provided with the electrode part 413 having the needle electrode 413 for generating positive ions and the electrode part 412 having the needle electrode 412a for generating negative ions, which are separated from each other. In addition, the ion generating part 410 is so attached that the needle electrodes 412a and 413a are arranged in the horizontal direction (lateral direction).

The fan 3 allows the air to flow from the feed port 74 toward the outlet 14 in the direction indicated by the reference code B. The direction of the reference code B, however, is to conceptually indicate the substantial direction of the air. More precisely, the air pushed out by the blades 30 flows in the upper diagonal direction (upper left direction in FIG. 8, lower diagonal direction in the state where the ion generating apparatus 100 is installed) from the feed port 74 toward the outlet 14.

The ion sensor 414 is so arranged that the angle α of the virtual line L1 defining the spacing distance between the needle electrode 412a and the ion sensor 414 is larger than 90 degrees and smaller than 180 degrees with respect to the virtual line L2 defining the spacing distance between the needle electrode 412a and the needle electrode 413a.

Accordingly, when the needle electrodes 412a and 413a are arranged horizontally (in the lateral direction) with each other, the ion sensor 414 is located not directly above (directly below in the state where the ion generating apparatus 100 is installed) the needle electrode 412a but in the upper diagonal direction (lower diagonal direction in the state where the ion generating apparatus 100 is installed) from the needle electrode 412a. Thus, in the case where the direction of the air coming out from the fan 3 is not in the vertical direction (longitudinal direction) but in the direction diagonal to the vertical direction, the ion sensor 414 can be arranged at the downstream side of the needle electrode 412a for ion detection along the air flowing direction and can be positioned away from the needle electrode 413a not for ion detection, allowing precise detection of ion concentration.

In the example described above, the ion generating unit has the lid 421. The structure for removably attaching the ion generating part 410 is, however, not limited to the example described above. Another example will be described below.

Figure 9:
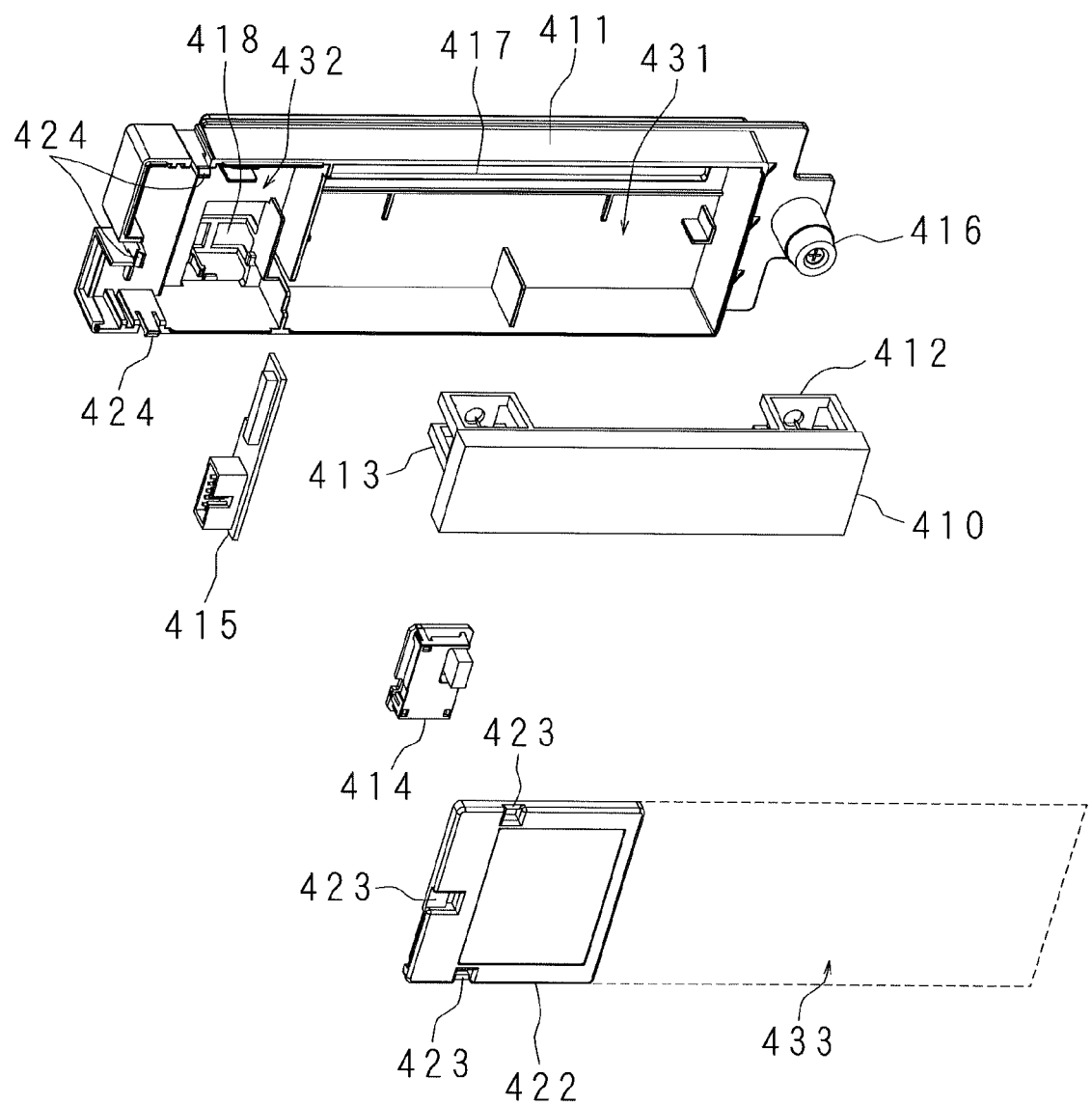
FIG. 9 is an exploded perspective view as the second example of the ion generating unit according to an embodiment of the invention.

FIG. 9 is an exploded perspective view as the second example of the ion generating unit 41 according to the present embodiment. As illustrated in FIG. 9, in the second example, the lid 421 is not provided. The ion generating unit 41 includes an opening 433 for removing the ion generating part 410 from the housing 411 without the exposure of the ion sensor 414. If abnormality occurs at the ion generating unit 410 while the ion sensor 414 operates normally, the ion generating unit 410 is removed from the opening 433 without exposure of the ion sensor 414. After replacing the ion generating part 410, the ion generating part 410 is inserted into the opening 433 to be attached to the housing 411, and the ion generating unit 41 with the replaced ion generating part 410 is mounted to the ion generating apparatus 100. This allows only the ion generating part 410 to be replaced without replacement of the normal ion sensor 414, thereby preventing the cost from unnecessarily increasing.

Figure 10:
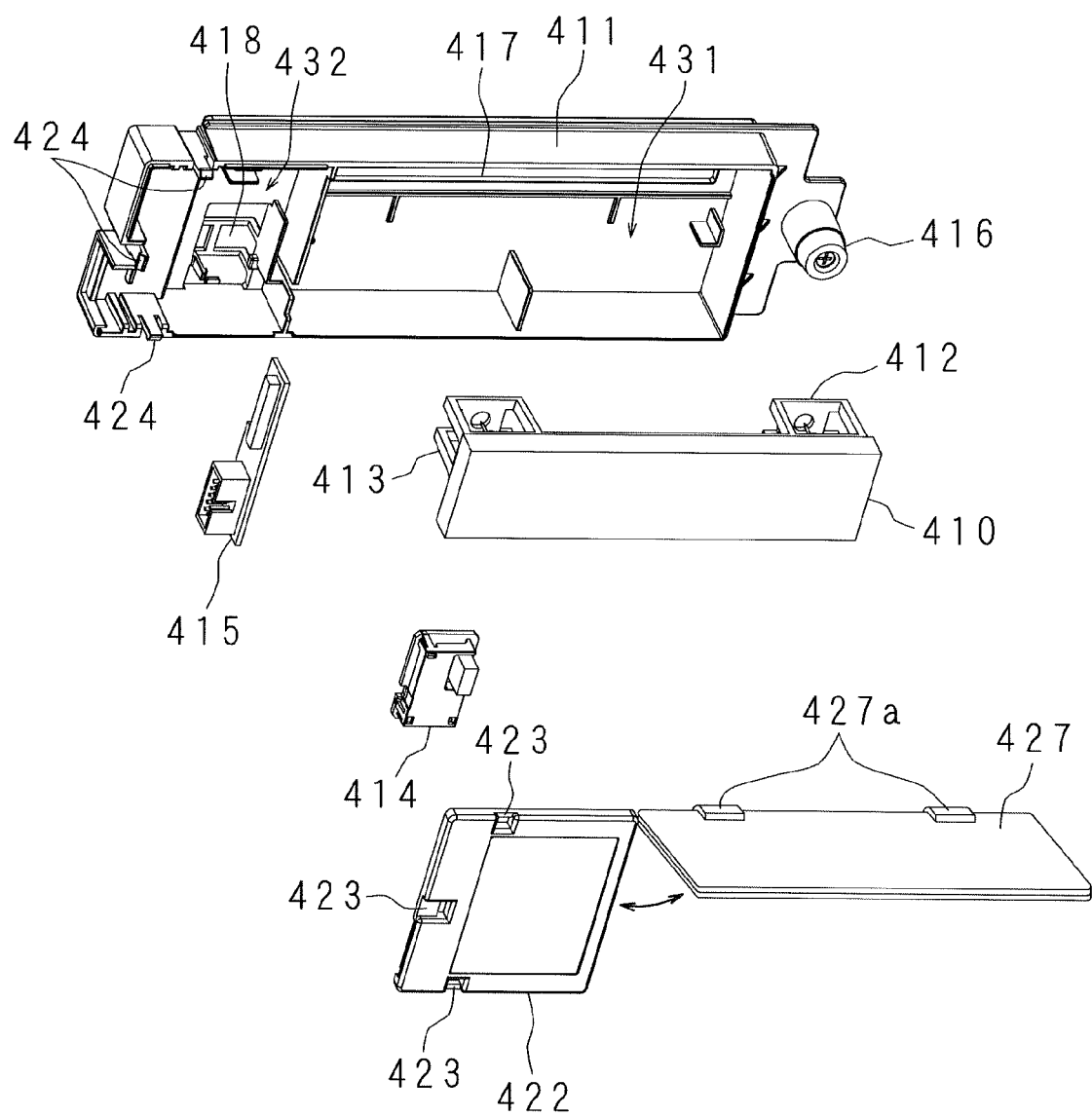
FIG. 10 is an exploded perspective view as the third example of the ion generating unit according to an embodiment of the invention.

FIG. 10 is an exploded perspective view as the third example of the ion generating unit 41 according to the present embodiment. As illustrated in FIG. 10, a lid 427 may be fixed to the housing 411 in a rotatable manner with a hinge 427a, and the lid 427 may be opened or closed as indicated by the arrow shown in FIG. 10. If abnormality occurs at the ion generating part 410 while the ion sensor 414 operates normally, the lid 427 may be opened to replace the ion generating part 410 without exposure of the ion sensor 414. Thereafter the lid 427 is closed and the ion generating unit 41 with the replaced ion generating part 410 is mounted to the ion generating apparatus 100. This allows only the ion generating part 410 to be replaced without replacement of the normal ion sensor 414, thereby preventing the cost from unnecessarily increasing.

FIG. 11 is an exploded perspective view as the fourth example of the ion generating unit 41 according to the present embodiment. As illustrated in FIG. 11, in place of the lid 421 and cover 422 in the first example shown in FIG. 6, a structure including a frame 435 and a lid 436 slidably attached to the frame 435 having substantially the same dimensions as those of the lid 421 and cover 422 may also be employed. The frame 435 is provided with a ridge (not illustrated) for making the lid 436 slide. By inserting the edge of the lid 436 in the longitudinal direction into the ridge, the lid 436 can be attached to the housing 411 so as to be opened or closed. In such as case, the frame 435 is secured to the housing 411 in a manner not easily removable.

If abnormality occurs at the ion generating unit 410 while the ion sensor 414 operates normally, the lid 436 is slid open and the ion generating part 410 is replaced without exposure of the ion sensor 414. Thereafter, the lid 436 is slid closed and the ion generating unit 41 with the replaced ion generating part 410 is mounted to the ion generating apparatus 100. This allows only the ion generating part 410 to be replaced without replacement of the normal ion sensor 414, thereby preventing the cost from unnecessarily increasing.

While the embodiment described above employed the structure including multiple ion generating units and outlets, the present invention is not limited thereto. It is also possible to have one ion generating unit and one outlet.

Though, in the present embodiment, an ion generating apparatus was described as an example of an electric device, the present embodiment is not limited to the ion generating apparatus but may also be applied to electric devices such as an air purifier, an air conditioner, a fan heater, a humidifier, a dehumidifier, a refrigerator, a sterilizer and the like. In each of the electric devices described above, the ion generating unit may be attached in a removable manner. Technical features described in the above embodiments of the present invention can form a new technical solution in combination with each other.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. An ion generating unit provided with
a housing accommodating an ion generating part and an ion sensor detecting an ion generated at the ion generating unit, comprising
an opening configured to remove the ion generating part from the housing with the ion sensor being accommodated in the housing,
wherein the ion generating part has an electrode for generating ions,
the ion sensor has a sensor plane for detecting ions, and
the housing accommodates the ion sensor with the sensor plane exposed at a part of the housing, and accommodates the ion generating part with the electrode protruding from the part.

2. The ion generating unit according to claim 1, further comprising
a lid configured to cover the opening in such a manner as to be removable or opened/closed.

3. The ion generating unit according to claim 2, further comprising
a cover configured to cover the housing in which the ion sensor is accommodated in such a manner as not to be easily removed or easily opened and closed.

4. The ion generating unit according to claim 1, further comprising
a cover configured to cover the housing in which the ion sensor is accommodated in such a manner as not to be easily removed or easily opened and closed.

5. The ion generating unit according to claim 1, wherein
the ion generating part is provided with an electrode for generating a positive ion and an electrode for generating a negative ion separated from each other, and
the ion sensor is so provided that a virtual line defining a spacing distance between the ion sensor and one electrode for ion detection has an angle larger than 90 degrees but smaller than 180 degrees with respect to a virtual line defining a spacing distance between said one electrode and another electrode.

6. An electric device comprising the ion generating unit according to claim 1, wherein
the ion generated at the ion generating unit is discharged from an outlet.

* * * * *